US00PP11722P

United States Patent [19]

van Andel

[11] Patent Number: Plant 11,722

[45] Date of Patent: Dec. 26, 2000

[54] ALSTROEMERIA PLANT NAMED 'STAPRIRANA'

[75] Inventor: Jacob van Andel, Aalsmeer, Netherlands

[73] Assignee: Van Staaveren B.V., Aalsmeer, Netherlands

[21] Appl. No.: 09/226,317

[22] Filed: Jan. 6, 1999

[51] Int. Cl.[7] ..... A01H 5/00

[52] U.S. Cl. ..... Plt./309

[58] Field of Search ..... Plt./309

[56] References Cited

PUBLICATIONS

UPOV–ROM, 1999/02, Plant Variety Database, GTI Jouve Retrieval Software, 2 citations for 'Staprirana' and 1 citation for 'Stalsimo'.

*Primary Examiner*—Howard J. Locker
*Attorney, Agent, or Firm*—Christie, Parker & Hale, LLP

[57] ABSTRACT

A new and distinct Alstroemeria plant variety producing flowers of good quality and attractive coloration.

1 Drawing Sheet

BACKGROUND OF THE INVENTION

The present invention relates to a new and distinct variety of Alstroemeria which is a cross of two unnamed, undistributed seedlings; namely, 92D66-1 as seed parent and 90F141-2 as pollen parent. The varietal denomination of the new variety is 'Staprirana'.

The first act of asexual reproduction of 'Staprirana' was in Aalsmeer, The Netherlands, by propagation by dividing the rhizomes. Asexual reproduction by dividing rhizomes through successive generations in Aaslmeer, The Netherlands, has demonstrated that the combination of characteristics as herein disclosed for 'Staprirana' are firmly fixed and retained through successive generations.

SUMMARY OF THE INVENTION

The new variety of Alstroemeria, 'Staprirana', produces large flowers.

DESCRIPTION OF ILLUSTRATION

The new variety of Alstroemeria hybrid is illustrated in the accompanying illustration, which shows typical flower characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Aalsmeer, The Netherlands. Color designations indicated are in accordance with The Royal Horticultural Society Color Chart by color plate designations.

'Staprirana' has not been observed under all possible environmental conditions. Phenotypic expression may vary with variations in environment such as temperature, light intensity, day length and growing and cultural conditions.

Botanical classification:
- *Family.*—Amaryllidaceae.
- *Genus.*—Alstroemeria sp.

Plant:
- *Form.*—Bush.
- *Shape.*—Upright.
- *Height.*—About 20 to 45 cm.
- *Main stem.*—About 35 cm.

- *Internode length.*—About 0.5–2 cm.
- *Growth.*—Vigorous.
- *Strength.*—Strong.
- *Blooming habit.*—Continuous.
- *Rhizomes.*—Age of plant about 1 to 2 years. Color: Near 155D. Size: About 10 to 30 cm.

Foliage:
- *Number of leaves.*—About 10 to 20 per stem.
- *Size of leaf.*—Length: About 2 to 10 cm. Width: About 1 to 3 cm.
- *Shape of leaf.*—Elliptic.
- *Margin.*—Straight, entire.
- *Texture.*—Glossy.
- *Color.*—Upper side: Near 137A. Underside: Near 137C.

Flower:
- *Blooming habit.*—Continuous, profusely throught the year.
- *Size (when first anthers release pollen).*—Diameter: About 6 cm. Depth: About 5 cm.
- *Borne.*—Umbel-shaped cluster; about 3 to 6 blooms.
- *Shape or form.*—When bloom first opens: Cup. When bloom matures: Cup.
- *Fragrance.*—None.
- *Lasting quality.*—On plant: About 4 weeks. As cut flower: About 18–20 days.
- *Tepalage.*—Number of tepals: About 6. Arrangement: 2 concentric circles of 3 tepals. Shape: Obovate. Margin: Minutely crimped. Apex: Pointed. Texture: Soft. Appearance: Velvety.
- *Color.*—Outer tepals: Upper surface — Base near 2D, body near 2D with area of 39A in central portion of tepal, about 0–5 spots, spots near 185A in coloration; Under surface — body near 2D, with area of near 39A in central portion of tepal, and 143A toward extreme distal end of tepal. Inner lateral tepals: Upper surface — Base near 2D, body near 2D with central area of near 13A and small area of near 39A distal to central area, about 20–30 spots, spots near 185A in coloration; Under surface — Base near 2D, body near 2D with central area of near 13A and small area near 39A distal to central area. Inner median tepal: Upper surface — Base near 2D, body near 2D and 2B, with larger area of near 39A extending longitudinally along the length of central portion of tepal, about 3–10 spots, spots near 185A; Under surface coloration is similar to that of upper surface.

Flower stem:

*Peduncle length.*—About 1 to 5 cm.

*Color.*—Near 137B.

*Strength.*—Strong, erect.

*Discoloration.*—No discoloration after full bloom, not hairy.

*Persistence.*—Flower does not hang on and dry.

*Disease resistance.*—No special susceptibility or resistance to disease has been observed.

Bud:

*Size.*—Diameter: About 1 to 2 cm. Depth or length: About 2 to 4 cm.

*Form.*—Pear-shaped.

*Rate of opening.*—Fast.

*Color of tepals when tepals first divide.*—Near 2D and 143A.

*Color of tepals when tepals begin to unfurl.*—Near 2D and 143A.

Reproductive organs:

*Stamen.*—Number: About 6. Arrangement: Side by side around the style.

*Anthers.*—Size: About 8 to 10 mm. Color: Near 138B.

*Filaments.*—Length: 5 cm. Color: Near 39A.

*Pollen.*—Color: Near 166C.

*Pistils.*—1. Styles: Length about 4 to 5 cm. Color: Near 39A.

*Stigmas.*—Color: Near 39A.

Fruit:

*Fertile.*—Yes.

*Shape.*—Round.

*Color at maturity.*—Near 163A.

I claim:

1. A new and distinct Alstroemeria plant of the variety substantially as shown and described.

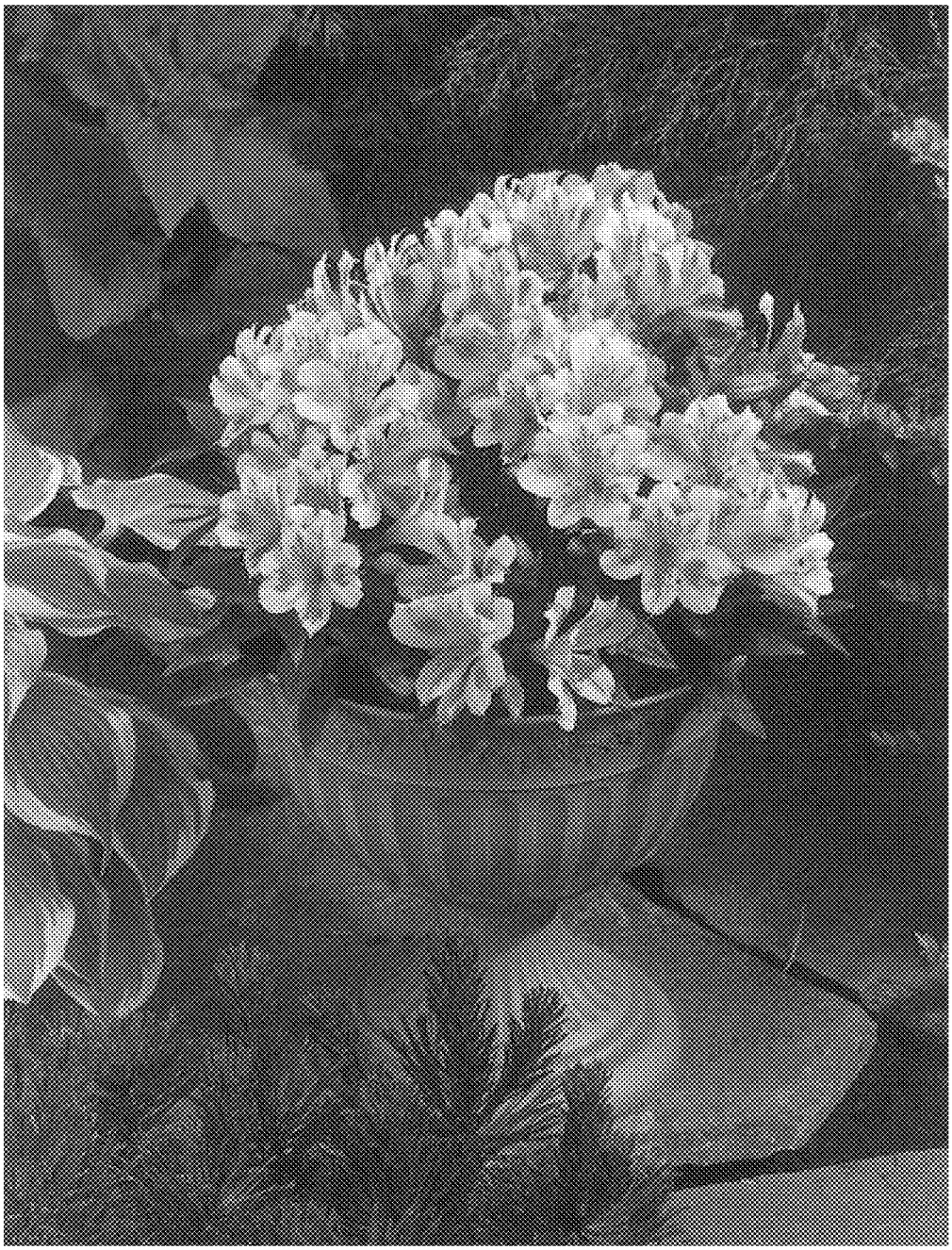

* * * * *